(12) United States Patent
Bowden

(10) Patent No.: US 6,516,800 B1
(45) Date of Patent: Feb. 11, 2003

(54) NEONATAL PATIENT VENTILATOR CIRCUIT

(75) Inventor: Kevin D. J. Bowden, Orangeville (CA)

(73) Assignee: O-Two Systems International Inc. (CA)

( * ) Notice: Subject to any disclaimer, the term of this patent is extended or adjusted under 35 U.S.C. 154(b) by 95 days.

(21) Appl. No.: 09/648,144

(22) Filed: Aug. 25, 2000

(51) Int. Cl.⁷ .............................................. A61M 16/00
(52) U.S. Cl. ............................. 128/204.18; 128/205.24; 128/204.23
(58) Field of Search ....................... 128/204.18, 203.22, 128/205.11, 204.21, 204.23, 205.24, 911, 912

(56) References Cited

U.S. PATENT DOCUMENTS

| | | | |
|---|---|---|---|
| 3,672,366 A | | 6/1972 | Burchell et al. .......... 128/145.8 |
| 3,964,476 A | * | 6/1976 | Palleni ..................... 128/145.6 |
| 4,836,198 A | * | 6/1989 | Gates ..................... 128/205.18 |
| 5,133,345 A | * | 7/1992 | Lambert ................ 128/202.16 |
| 5,140,983 A | * | 8/1992 | Jinotti .................... 128/205.24 |
| 5,392,770 A | * | 2/1995 | Clawson et al. ....... 128/203.27 |
| 5,425,358 A | * | 6/1995 | McGrail et al. ....... 128/204.18 |
| 5,617,847 A | * | 4/1997 | Howe .................... 128/204.23 |
| 5,687,709 A | * | 11/1997 | Akerberg ............... 128/203.12 |
| 6,102,038 A | * | 8/2000 | DeVries ................. 128/204.23 |
| 6,283,122 B1 | * | 9/2001 | Adahan ................. 128/204.23 |

FOREIGN PATENT DOCUMENTS

EP 0 990 448 A 4/2000

* cited by examiner

Primary Examiner—Aaron J. Lewis
Assistant Examiner—Mital Patel
(74) Attorney, Agent, or Firm—Mark Kusner; Michael A. Jaffe

(57) ABSTRACT

A disposable neonatal patient ventilator circuit for an automatic ventilator. All components that are exposed to contamination from the patient are packaged together in a disposable unit external to the automatic ventilator. The automatic ventilator has a receptacle with a pressurized breathable gas supply port, a breathing control circuit port, and preferably a patient monitoring port. The disposable neonatal resuscitator unit matches the ports on the automatic ventilator with a removable plug having a pressurized breathable gas supply connector mating the gas supply port of the receptacle; a breathing control circuit connector mating the control circuit port of the receptacle and a monitoring connector mating the monitoring port of the receptacle. A patient interface such as a tracheal insertion tube or mouth insertion manifold has an inlet and an outlet each in flow communication with the neonatal patient's airway. A gas supply conduit communicates between the patient interface inlet and gas supply connector of the plug. Breathing control valve, in communication with the interface outlet and with the breathing control connector of the plug, serves to exhaust exhaled pressurized gas from the patient airway when open and retaining pressurized gas in the patient airway when closed, in response to open and close signals communicated by the automatic ventilator via the breathing control connector of the plug.

4 Claims, 2 Drawing Sheets

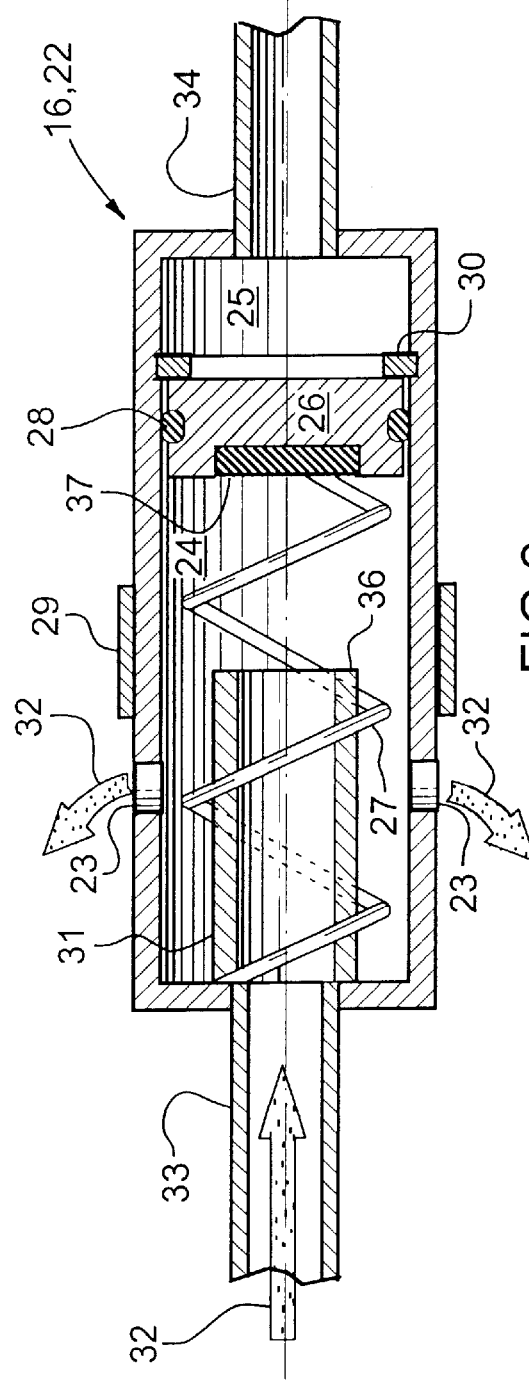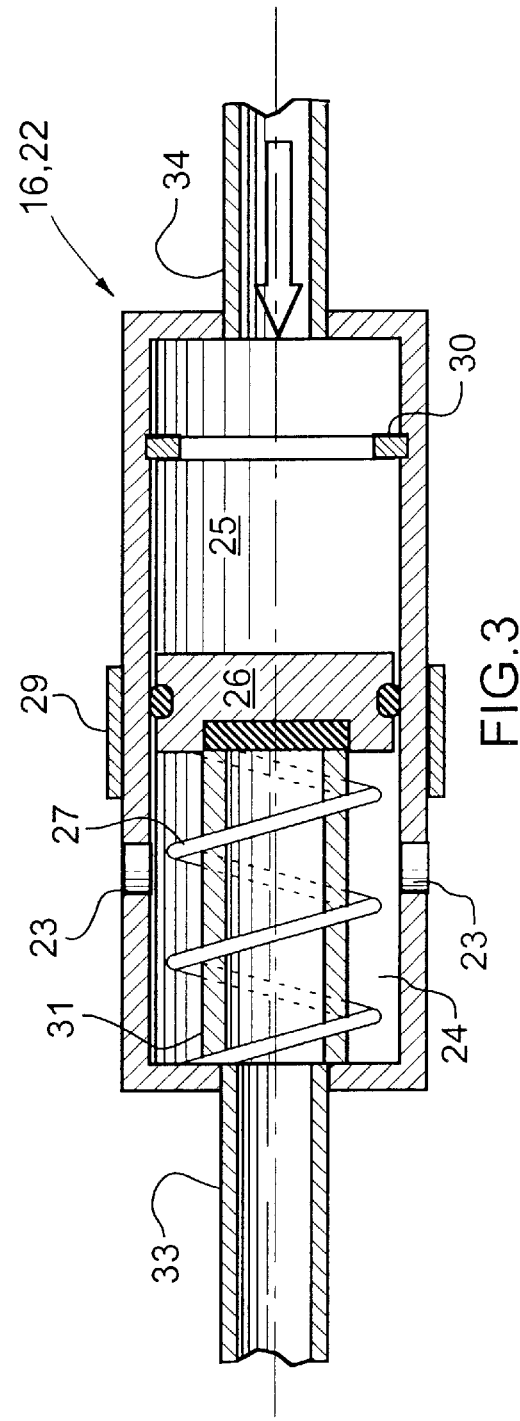

NEONATAL PATIENT VENTILATOR CIRCUIT

TECHNICAL FIELD

The invention relates to a disposable neonatal patient ventilator circuit for an automatic ventilator where all components that are exposed to contamination from the patient (including a disposable breathing control valve) are packaged together in a disposable unit external to the automatic ventilator.

BACKGROUND OF THE ART

Ventilation of neonatal infants presents a number of difficulties, which are not encountered with adults. The lungs of newborns or premature babies are liable to collapse and due to their unique makeup, once the lungs are collapsed neonatal lungs are extremely difficult if not impossible to re-inflate. As a result, infant ventilation includes maintaining a constant patient airway pressure to prevent collapse, and automatic ventilation improves infant mortality rates significantly over manual ventilation.

Ventilation of premature infants usually involves the supply of pressurized gas at a constant flowrate of between 0.5 to 5.0 liters per minute. Automatic ventilators are preferably utilized by this function however quite often the conventional method of infant ventilation merely involves inflating the infant's lung with pressurized breathable gas through a conduit connected to a mouth piece and deflation manually by alternatively placing the operator's thumb and removing the operator's thumb from an exhaust port.

Due to the critical nature of maintaining constant airway pressure, the danger of under inflation and irreversible lung collapse, as well as the danger of overinflating the infant's lungs causing lung damage or distention of the stomach, this commonly used manual method is very unsatisfactory. Preferably, automatic ventilators should be used for all patients including neonatal patients. However, the perceived high cost often inhibits adoption of automatic ventilators.

It is an object of the invention to provide a modified neonatal patient ventilator circuit for use in association with an automatic ventilator that facilitates the provision of constant positive airway pressure.

It is a further object of the invention to provide a neonatal patient ventilator circuit wherein all components that are exposed to potentially contaminated exhaled air from the infant can be packaged in a single unit that is inexpensive enough to be disposable and eliminates the cost and downtime associated with sterilizing components of the automatic ventilator.

Further objects of the invention will be apparent from review of the disclosure and description of the invention below.

DISCLOSURE OF THE INVENTION

The invention relates to an inexpensive disposable neonatal patient ventilator circuit for use with an automatic ventilator. All components that are exposed to contamination from the patient are packaged together in a disposable unit external to the automatic ventilator. The automatic ventilator has a receptacle with a pressurised breathable gas supply port, a breathing control circuit port, and preferably a patient monitoring port. The disposable neonatal resuscitator unit matches the ports on the automatic ventilator with a removable plug having a pressurised breathable gas supply connector mating the gas supply port of the receptacle; a breathing control circuit connector mating the control circuit port of the receptacle and a monitoring connector mating the monitoring port of the receptacle. A patient interface, such as an endotracheal insertion tube or mouth insertion manifold, has an inlet and an outlet each in flow communication with the neonatal patient's airway. A gas supply conduit communicates between the patient interface inlet and gas supply connector of the plug. Breathing control valve, in communication with the interface outlet and with the breathing control connector of the plug, serves to exhaust exhaled pressurised gas from the patient airway when open and retaining pressurised gas in the patient airway when closed, in response to open and close signals communicated by the automatic ventilator via the breathing control connector of the plug.

Further details of the invention and its advantages will be apparent from the detailed description and drawings included below.

BRIEF DESCRIPTION OF THE DRAWINGS

In order that the invention may be readily understood, one preferred embodiment of the invention will be described by way of example, with reference to the accompanying drawing wherein:

FIG. 2 is a cross-sectional view through the breathing control valve in the open (exhale) position; and FIG. 3 is a cross-sectional view through the breathing control valve in the closed (inhale) position; and Further details of the invention will become apparent from the detailed description presented below.

DETAILED DESCRIPTION OF PREFERRED EMBODIMENTS

Figure 1:
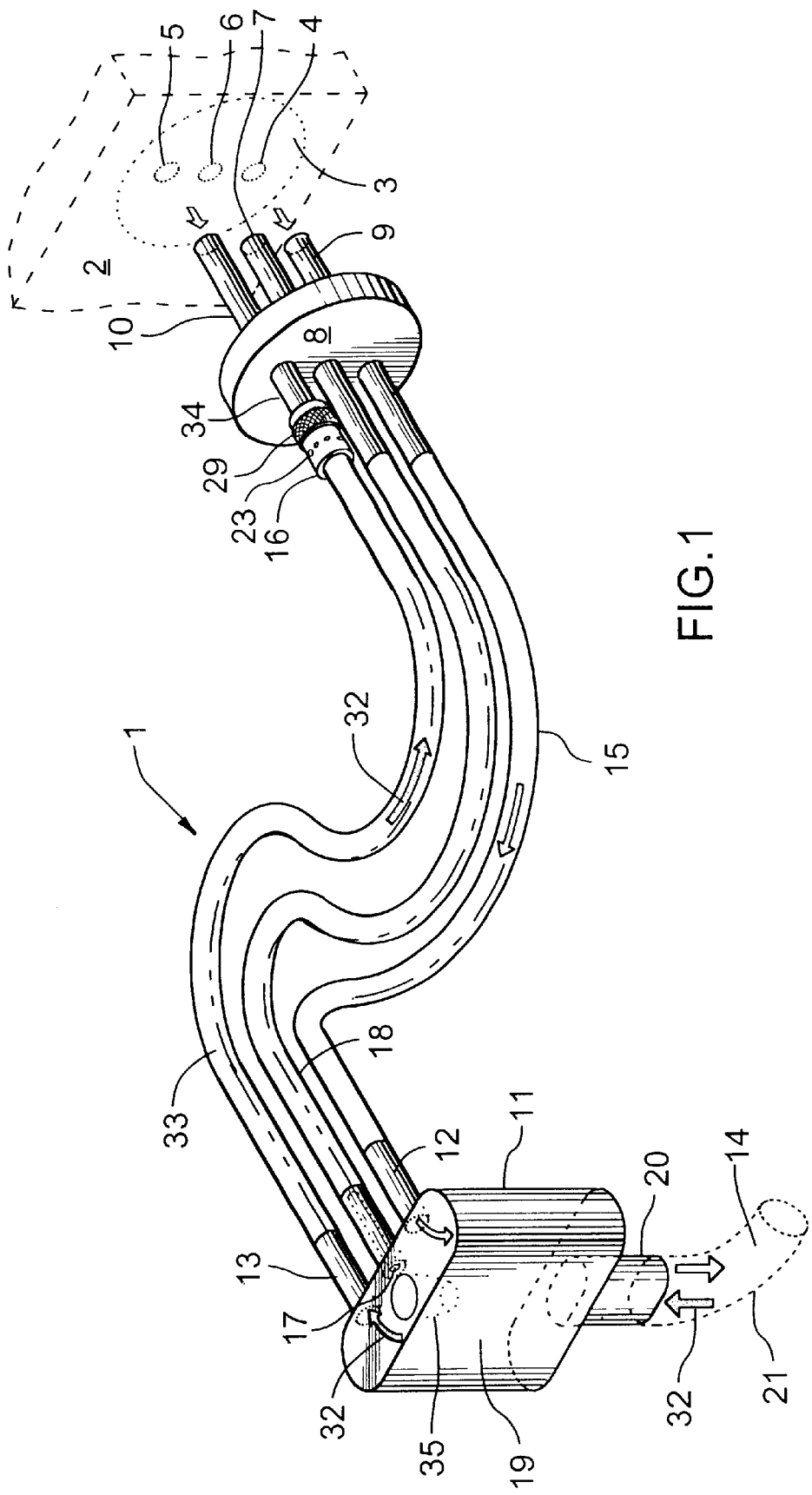
FIG. 1 is a perspective view of a disposable neonatal resuscitator unit according to the invention with removable plug and mating receptacle, breathing control valve, and patient interface manifold including breathable gas supply conduit, exhalation conduit, and patient airway monitoring conduit.

FIG. 1 illustrates one embodiment of the neonatal patient ventilator circuit 1 wherein all components that may be contaminated by the patient's exhaled breath are packaged together in a disposable unit. The disposable unit 1 works together with an automatic ventilator 2 that has been modified accordingly to accept the plug 8 of the device 1. Of note, the breathing control valve 16 is also included in the disposable patient resuscitator device 1 thereby eliminating the need to sterilize any component of the automatic ventilator 2. In this manner the automatic ventilator 2 is always available for service and need not be disassembled for sterilization by users.

With reference to FIG. 1, the disposable neonatal patient ventilator circuit 1 has a removable plug 8 which mates with a receptacle 3 of the automatic ventilator 2. The receptacle 3 includes a pressurized breathable gas supply port 4 and a breathing control circuit port 5. The automatic ventilator 2 provides pressurized gas through the breathing circuit port 5 to control the operation of the breathing control valve 16 as explained in detail below.

The removable plug 8 has a pressurized breathable gas supply connector 9, which matches the gas supply port 4 of the receptacle 3. In a like manner, the breathing control circuit connector 10 matches the control circuit port 5 of the receptacle 3. Optionally, the receptacle 3 includes a patient airway monitoring port 6 and the plug 8 includes a monitoring connector 7 matching the monitoring port 6 of the receptacle 3. The monitoring port 6 of the automatic ventilator 2 can be connected with a circuit that provides automatic alarms or visual pressure gauges to monitor the patient's condition.

The patient interface has an inlet 12 for pressurized gas and an outlet 13 for exhausting exhaled air 32. The inlet 12 and outlet 13 are each in flow communication with the patient's airway 14. The patient interface can be in the form of a hollow plastic manifold 11 as shown with internal chamber 19 in flow communication with a patient airway port 20 or mouthpiece 20. As illustrated, the inlet 12 and outlet 13 are each in flow communication with the internal chamber 19 of the manifold. Optionally, the manifold 11 can include a tracheal tube 21 when intubation is required.

The breathable gas is supplied in tidal volumes by the automatic ventilator 2 via the gas supply conduit 15 communicating between the interface inlet 12 and the gas supply connector 9 of the plug 8. The automatic ventilator 2 provides tidal volumes at the flow rate desired in an automatic manner well known in the prior art. For example, an automatic ventilator which can be modified to serve this purpose is illustrated in U.S. Pat. No. 6,055,981 to Bowden et al. issued May 2, 2000. The automatic ventilator 2 delivers pressurized breathable gas via the gas supply port 4 and at the same time the automatic ventilator 2 provides a control flow of gas via the breathing control port 5 to close the breathing control valve 16 preventing exhalation of air from the patient via the interface outlet 13.

The breathing control valve 16 communicates between the interface outlet 13 and the breathing control connector 10 of the plug 8 via the exhalation conduit 33. Exhaled pressurized gas 32 from the patient's airway 14 is exhausted during the exhale stage of the breathing cycle, as illustrated in FIG. 2, from the breathing control valve 16 when the valve 16 is open. As shown in FIG. 3, the breathing control valve 16 retains pressurized gas within the patient's airway 14 during the inhale stage of the breathing cycle when the breathing control valve 16 is closed.

Pressurized gas delivered through the breathing control connector 10 and breathing control conduit 34 moves the piston 26 of the valve 16 against the force of spring 27 to pressurize the control chamber 25 and contain pressurized gas (delivered via conduit 15) within the patient airway 14 as a result of closing the breathing control valve 16. The neoprene piston seal 37 engages the valve seat 36 to seal the end of tube 31 thus preventing gas from escaping through the exhaust ports 23.

Referring to FIG. 1, the patient interface manifold 11 includes a monitoring aperture 17 in communication with the patient's airway 14. A monitoring conduit 18 communicates between the patient monitoring aperture 17 and the monitoring connector 7 of the plug 8. Patient airway pressure can be detected and shown on gauges within the automatic ventilator 2 or can trigger audible or visual alarms within the automatic ventilator in the event that pressure is detected beyond a predetermined optimal range. A duckbill valve 35 may also be provided in the top surface of the manifold 11 in order to insert probes or otherwise monitor the patient's condition.

The details of the breathing control valve 16 are shown in FIGS. 2 and 3. As mentioned above, FIG. 2 shows the open or exhale position wherein exhaled gas 32 from the patient can be exhausted through exhaust ports 23. FIG. 3 shows the valve 16 in a closed or inhale position wherein pressurized gas is retained in the patient's airway 14 during the inhale portion of the breathing cycle. The valve 16 includes a hollow valve housing 22 with exhaust ports 23. The housing 22 is divided into an exhalation chamber 24 and a control chamber 25 disposed on opposing sides of sealed sliding piston 26. The piston 26 is sealed with sliding O-rings 28 Gas 32 is prevented from escaping through the exhaust ports 23 when the piston seal 37 engages the valve seat 36 to seal the end of tube 31.

In the embodiment shown, the motion of the piston 26 is restrained by stop ring 30 in the open position and by valve seat 36 in the closed position shown in FIG. 3. The piston 26 is biased towards the open position FIG. 2 wherein the exhalation chamber 24 is in flow communication with the exhaust ports 23. As a result, the patient is permitted to exhale gas from the patient airway 14. The piston 26 as shown in FIG. 3 is forced against the spring 27 to a closed position when control pressurized gas pressurizes the control chamber 25 moves the piston 26 against the biasing force of spring 27. The exhalation chamber 24 of the valve 16 is in flow communication with the patient interface outlet 13 via the exhalation conduit 33. The control chamber 25 is in flow communication with pressurized gas conducted by the automatic ventilator 2 via the breathing control connector 10 of the plug 8 and breathing control conduit 34.

To control the rate of exhaled gas and gas pressure within the patient airway 14 during exhalation, the exhaust ports 23 can be restricted by simply sliding the ring 29 on the valve 16 exterior to partially cover the exhaust ports 23. Other variable flow restriction means can also be incorporated to the same end such as including a variable flow As a result of packaging the plug 8 with connectors 7, 9, 10 and control valve 16 together with conduits 15, 18, 33 and patient interface, the invention provides a simple, inexpensive and disposable neonatal patient ventilator circuit that eliminates the need to sterilize and maintain the automatic ventilator 2 before use on another patient.

The embodiments of the invention in which an exclusive property or privilege is claimed are defined as follows:

1. In an automatic ventilator, the automatic ventilator having a receptacle with: a pressurized breathable gas supply port; and a breathing control circuit port, a neonatal patient ventilator circuit comprising:

a removable plug with: a pressurized breathable gas supply connector adapted to releasably engage the gas supply port of the receptacle; and a breathing control circuit connector adapted to releasably engage the control circuit port of the receptacle;

a patient interface having an inlet and an outlet each adapted to be in flow communication with the patient's airway;

a gas supply conduit communicating between the interface inlet and gas supply connector of the plug; and breathing control valve means, in communication with the interface outlet and with the breathing control connector of the plug, for exhausting pressurized gas from the patient airway when open and retaining pressurized gas in the patient airway when closed, in response to open and close signals communicated via the breathing control connector of the plug, wherein the breathing control valve means comprise: a hollow valve housing including an exhaust port, the housing including an exhalation chamber and a control chamber disposed on opposing sides of a piston, the piston operating between an open position wherein the exhalation chamber is in flow communication with the exhaust port and a closed position, wherein: the flow communication between the exhalation chamber and the exhaust port is impeded by the piston; the exhalation chamber is in flow communication with the patient interface outlet; and the control chamber is in flow communication with pressurized gas conducted via the breathing control connector of the plug;

the breathing control valve means further comprising: piston biasing means for urging the piston to the open position against the force of pressurized gas within the control chamber.

2. A neonatal patient ventilator circuit in accordance with claim 1 wherein: the receptacle includes a patient airway monitoring port; the plug includes a monitoring connector adapted to releasably engage the monitoring port of the receptacle; the patient interface includes a monitoring aperture adapted to be in communication with the patient airway; and the neonatal patient ventilator circuit further comprises a monitoring conduit communicating between the patient monitoring aperture and monitoring connector.

3. A neonatal patient ventilator circuit in accordance with claim 1 wherein the patient interface comprises a manifold having an internal chamber in flow communication with a patient's airway port, wherein said inlet and outlet are each in flow communication with the internal chamber.

4. A neonatal patient ventilator circuit in accordance with claim 3 wherein the manifold includes a tracheal insertion tube.

* * * * *